(12) United States Patent
Dearden et al.

(10) Patent No.: US 12,194,290 B2
(45) Date of Patent: Jan. 14, 2025

(54) ELECTRODE LEADS HAVING MULTI-APPLICATION NERVE CUFFS AND ASSOCIATED SYSTEMS AND METHODS

(71) Applicant: The Alfred E. Mann Foundation for Scientific Research, Valencia, CA (US)

(72) Inventors: Brian Ralph Dearden, Pasadena, CA (US); Brian M. Shelton, Altadena, CA (US); Neil Talbot, La Crescenta, CA (US)

(73) Assignee: The Alfred E. Mann Foundation for Scientific Research, Valencia, CA (US)

( * ) Notice: Subject to any disclaimer, the term of this patent is extended or adjusted under 35 U.S.C. 154(b) by 406 days.

(21) Appl. No.: 17/463,611

(22) Filed: Sep. 1, 2021

(65) Prior Publication Data

US 2022/0062629 A1 Mar. 3, 2022

Related U.S. Application Data

(60) Provisional application No. 63/073,868, filed on Sep. 2, 2020.

(51) Int. Cl.
*A61N 1/05* (2006.01)
*A61N 1/36* (2006.01)

(52) U.S. Cl.
CPC ......... *A61N 1/0556* (2013.01); *A61N 1/3605* (2013.01)

(58) Field of Classification Search
CPC ................ A61N 1/0556; A61N 1/3605; A61N 1/36078; A61N 1/3611; A61N 1/05;
(Continued)

(56) References Cited

U.S. PATENT DOCUMENTS 4,573,481 A   3/1986 Bullara
4,602,624 A   7/1986 Naples et al.
(Continued)

FOREIGN PATENT DOCUMENTS

WO   WO 2008092246 A1   8/2008
WO   WO 2009045772 A1   4/2009
(Continued)

OTHER PUBLICATIONS

U.S. Appl. No. 17/463,630, filed Sep. 1, 2021.
(Continued)

*Primary Examiner* — Benjamin J Klein
*Assistant Examiner* — Daniel Tehrani
(74) *Attorney, Agent, or Firm* — Henricks Slavin LLP (57) ABSTRACT

An electrode that includes an elongate lead body and a nerve cuff. The nerve cuff may include a biologically compatible, elastic, electrically insulative cuff body configured to be circumferentially disposed around a nerve, first and second relatively wide electrically conductive contacts carried by the cuff body that are spaced from one another in the length direction and that extend in the width direction to such an extent that they extend completely around the cuff body inner lumen when the cuff body is in the pre-set furled shape, and a plurality of relatively narrow electrically conductive contacts carried by the cuff body that are spaced from one another in the width direction and are located between the first and second relatively wide electrically conductive contacts.

13 Claims, 9 Drawing Sheets

(58) Field of Classification Search
CPC ............... A61N 1/3606; A61N 1/0548; A61N 2007/0026; A61N 1/18
See application file for complete search history.

(56) References Cited

U.S. PATENT DOCUMENTS

| | | | |
|---|---|---|---|
| 4,940,065 A | 7/1990 | Tanagho et al. |
| 5,251,634 A | 10/1993 | Weinberg |
| 5,400,784 A | 3/1995 | Durand et al. |
| 5,439,485 A | 8/1995 | Mar et al. |
| 5,487,756 A | 1/1996 | Kallesoe et al. |
| 5,634,462 A | 6/1997 | Tyler et al. |
| 5,919,220 A | 7/1999 | Stieglitz et al. |
| 6,066,165 A | 5/2000 | Racz |
| 6,210,339 B1 | 4/2001 | Kiepen et al. |
| 6,292,703 B1 | 9/2001 | Meier et al. |
| 7,383,090 B2 | 6/2008 | O'Brien et al. |
| 7,794,256 B1 | 9/2010 | Sochor |
| 7,809,442 B2 | 10/2010 | Bolea et al. |
| 7,996,092 B2 | 8/2011 | Mrva et al. |
| 8,116,882 B2 | 2/2012 | Kowalczewski |
| 8,155,757 B1 | 4/2012 | Neisz et al. |
| 8,224,449 B2 | 7/2012 | Carbunaru et al. |
| 8,311,645 B2 | 11/2012 | Bolea et al. |
| 8,340,785 B2 | 12/2012 | Bonde et al. |
| 8,660,665 B2 | 2/2014 | Walter et al. |
| 8,792,973 B2 | 7/2014 | Moran et al. |
| 8,934,992 B2 | 1/2015 | Johnson et al. |
| 9,186,511 B2 | 11/2015 | Bolea |
| 9,227,053 B2 | 1/2016 | Bonde et al. |
| 9,549,708 B2 | 1/2017 | Mercanzini et al. |
| 9,603,538 B2 | 3/2017 | Fisher et al. |
| 9,849,288 B2 | 12/2017 | Meadows et al. |
| 9,889,304 B2 | 2/2018 | Mercanzini |
| 9,931,045 B2 | 4/2018 | Brunnett et al. |
| 10,758,723 B2 | 9/2020 | Fang et al. |
| 11,833,348 B2 | 12/2023 | Brandt et al. |
| 2002/0198582 A1 | 12/2002 | Edell et al. |
| 2005/0070982 A1 | 3/2005 | Heruth et al. |
| 2005/0186829 A1 | 8/2005 | Balsells |
| 2006/0004430 A1 | 1/2006 | Rossing et al. |
| 2006/0030919 A1 | 2/2006 | Mrva et al. |
| 2007/0123765 A1 | 5/2007 | Hetke et al. |
| 2007/0185542 A1 | 8/2007 | Bolea et al. |
| 2008/0082137 A1* | 4/2008 | Kieval ............... A61N 1/36114 607/30 |
| 2008/0092246 A1 | 4/2008 | Shintani |
| 2008/0103545 A1 | 5/2008 | Bolea et al. |
| 2008/0172101 A1 | 7/2008 | Bolea et al. |
| 2009/0045772 A1 | 2/2009 | Cook et al. |
| 2009/0132042 A1 | 5/2009 | Hetke et al. |
| 2009/0210042 A1 | 8/2009 | Kowalczewski |
| 2010/0305674 A1 | 12/2010 | Zarembo et al. |
| 2010/0331933 A1 | 12/2010 | Carbunaru et al. |
| 2011/0066196 A1 | 3/2011 | Alexander et al. |
| 2011/0130815 A1 | 6/2011 | Gibson et al. |
| 2011/0154655 A1 | 6/2011 | Hetke et al. |
| 2011/0251473 A1 | 10/2011 | Moran et al. |
| 2011/0301665 A1 | 12/2011 | Mercanzini et al. |
| 2012/0089153 A1 | 4/2012 | Christopherson et al. |
| 2012/0150255 A1 | 6/2012 | Lindenthaler et al. |
| 2012/0154256 A1 | 6/2012 | Grover et al. |
| 2012/0277819 A1* | 11/2012 | Cowley ............... A61N 1/36053 607/45 |
| 2012/0316417 A1 | 12/2012 | Vetter |
| 2013/0030352 A1 | 1/2013 | Seymour et al. |
| 2013/0085361 A1 | 4/2013 | Mercanzini et al. |
| 2013/0090711 A1 | 4/2013 | Ramachandran et al. |
| 2013/0150938 A1 | 6/2013 | Carbunaru et al. |
| 2013/0304174 A1 | 11/2013 | Langhals et al. |
| 2014/0005763 A1 | 1/2014 | Cederna et al. |
| 2014/0058482 A1 | 2/2014 | Gupta et al. |
| 2014/0163659 A1 | 6/2014 | Boling |
| 2014/0188202 A1 | 7/2014 | Zarembo et al. |
| 2014/0228905 A1 | 8/2014 | Bolea |
| 2014/0303703 A1 | 10/2014 | Mercanzini et al. |
| 2015/0119673 A1 | 4/2015 | Pellinen et al. |
| 2015/0128413 A1 | 5/2015 | Vetter et al. |
| 2015/0157854 A1 | 6/2015 | Hetke et al. |
| 2015/0174396 A1 | 6/2015 | Fisher et al. |
| 2015/0224307 A1 | 8/2015 | Bolea |
| 2015/0374975 A1 | 12/2015 | Callegari et al. |
| 2016/0184581 A1 | 6/2016 | Bonde et al. |
| 2016/0199637 A1 | 7/2016 | Xu et al. |
| 2016/0287863 A1 | 10/2016 | Mercanzini et al. |
| 2016/0331326 A1 | 11/2016 | Xiang et al. |
| 2016/0331994 A1 | 11/2016 | Smith et al. |
| 2017/0266436 A1 | 9/2017 | Suwito et al. |
| 2017/0319846 A1 | 11/2017 | Plachta et al. |
| 2018/0117313 A1 | 5/2018 | Schmidt et al. |
| 2018/0132790 A1 | 5/2018 | Yao et al. |
| 2018/0221660 A1 | 8/2018 | Suri et al. |
| 2018/0318577 A1 | 11/2018 | Ng et al. |
| 2018/0318578 A1 | 11/2018 | Ng et al. |
| 2019/0060646 A1 | 2/2019 | Ng et al. |
| 2019/0069949 A1 | 3/2019 | Vrba et al. |
| 2019/0282805 A1 | 9/2019 | Schmidt et al. |
| 2020/0069935 A1 | 3/2020 | Johnson et al. |
| 2020/0083922 A1 | 3/2020 | Hong et al. |
| 2020/0146583 A1 | 5/2020 | Hestad et al. |
| 2020/0230412 A1 | 7/2020 | Rondoni et al. |
| 2020/0230421 A1 | 7/2020 | Zaidi et al. |
| 2020/0306526 A1 | 10/2020 | Doguet et al. |
| 2021/0205662 A1 | 7/2021 | Lu et al. |
| 2022/0088374 A1 | 3/2022 | Ackermann et al. |
| 2022/0313987 A1 | 10/2022 | Jenny et al. |
| 2023/0010510 A1 | 1/2023 | Brandt et al. |
| 2023/0241394 A1 | 8/2023 | Jenny et al. |
| 2024/0009452 A1 | 1/2024 | Jenny et al. |
| 2024/0058602 A1 | 2/2024 | Brandt et al. |
| 2024/0108883 A1 | 4/2024 | Trivedi et al. |

FOREIGN PATENT DOCUMENTS

| | | |
|---|---|---|
| WO | WO 2012154256 A1 | 11/2012 |
| WO | WO 2013188871 A1 | 12/2013 |
| WO | WO 2016039768 A1 | 3/2016 |
| WO | WO 2020182293 A1 | 9/2020 |
| WO | WO 2021108810 A1 | 6/2021 |

OTHER PUBLICATIONS

U.S. Appl. No. 17/710,570, filed Mar. 31, 2022.
PCT International Search and Written Opinion dated Jan. 5, 2022 for PCT App. Ser. No. PCT/US2021/048583.
U.S. Appl. No. 17/683,598, filed Mar. 1, 2022.
U.S. Appl. No. 17/463,611, filed Sep. 1, 2021, U.S. Pat. No. 2022/0062629 A1.
U.S. Appl. No. 17/463,630, filed Sep. 1, 2021, U.S. Pat. No. 11,833,348 B2.
U.S. Appl. No. 18/495,503, filed Oct. 26, 2023, U.S. Pat. No. 2024/0058602 A1.
U.S. Appl. No. 17/683,598, filed Mar. 1, 2022, U.S. Pat. No. 2022/0313987 A1.
U.S. Appl. No. 17/710,570, filed Mar. 31, 2022, U.S. Pat. No. 2023/0241394 A1.
U.S. Appl. No. 18/468,730, filed Sep. 17, 2023.
U.S. Appl. No. 18/186,927, filed Mar. 20, 2023, U.S. Pat. No. 2024/0009452 A1.

* cited by examiner

| contact | stim. | rtn. |
|---|---|---|
| 112b-1 | | X |
| 112b-2 | | |
| 112b-3 | | |
| 112b-4 | | |
| 112b-5 | | |
| 114b-1 | X | |
| 114b-2 | | |
| 114b-3 | | |
| 114b-4 | | |
| 114b-5 | | |
| 114b-6 | | |
| 114b-7 | | |
| 114b-8 | | |
| 114b-9 | | |
| 114b-10 | | |

*FIG. 18*

| contact | stim. | rtn. |
|---|---|---|
| 112b-1 | | |
| 112b-2 | | X |
| 112b-3 | | |
| 112b-4 | | |
| 112b-5 | | |
| 114b-1 | X | |
| 114b-2 | | |
| 114b-3 | | |
| 114b-4 | | |
| 114b-5 | | |
| 114b-6 | | |
| 114b-7 | | |
| 114b-8 | | |
| 114b-9 | | |
| 114b-10 | | |

*FIG. 18A*

| contact | stim. | rtn. |
|---|---|---|
| 112b-1 | | |
| 112b-2 | | |
| 112b-3 | | X |
| 112b-4 | | |
| 112b-5 | | |
| 114b-1 | | |
| 114b-2 | | |
| 114b-3 | X | |
| 114b-4 | | |
| 114b-5 | | |
| 114b-6 | | |
| 114b-7 | | |
| 114b-8 | | X |
| 114b-9 | | |
| 114b-10 | | |

*FIG. 18B*

ELECTRODE LEADS HAVING MULTI-APPLICATION NERVE CUFFS AND ASSOCIATED SYSTEMS AND METHODS

CROSS-REFERENCE TO RELATED APPLICATION

This application claims the benefit of U.S. Provisional Application No. 63/073,868, filed Sep. 2, 2020, and entitled "Multiple Application Nerve Cuffs," which is incorporated herein by reference.

BACKGROUND OF THE INVENTIONS

1. Field of Inventions

The present inventions relate generally to the treatment of obstructive sleep apnea by stimulating the hypoglossal nerve.

2. Description of the Related Art

Obstructive sleep apnea (OSA) is a highly prevalent sleep disorder that is caused by the collapse of or increase in the resistance of the pharyngeal airway, often resulting from a tongue obstruction. The obstruction of the upper airway is mainly caused by reduced genioglossus muscle activity during the deeper states of non-rapid eye movement (NREM) sleep. In some OSA patients, obstruction occurs predominantly during rapid eye movement (REM) sleep. This is known as REM OSA and has different cardiometabolic and neurocognitive risks. Obstruction of the upper airway causes breathing to pause during sleep. Cessation of breathing, in turn, causes a decrease in the blood oxygen saturation level, which is eventually corrected when the person wakes up and resumes breathing. The long-term effects of OSA include, but are not limited to, high blood pressure, heart failure, strokes, diabetes, headaches, and general daytime sleepiness and memory loss.

Some proposed methods of alleviating apneic events involve the use of neurostimulators to open the upper airway. Such therapy involves stimulating the nerve fascicles of the hypoglossal nerve (HGN) that innervate the intrinsic and extrinsic muscles of the tongue in a manner that prevents retraction of the tongue, which would otherwise close the upper airway during the inspiration portion of the respiratory cycle. In some instances, the trunk of the HGN is stimulated with a nerve cuff, including a cuff body and a plurality of electrically conductive contacts on the cuff body, that is positioned around the HGN trunk. The HGN trunk nerve cuff may be configured in such a manner that it can be used to selectively stimulate nerve fascicles which innervate muscles that extend the tongue, while avoiding other nerve fascicles, with what is predominantly radial vector stimulation. For example, the contacts may be axially aligned and circumferentially spaced around the perimeter of the HGN trunk. In other instances, a nerve cuff is placed on the branch of the HGN that is responsible for protruding the tongue (hereafter "HGN genioglossus muscle branch" or "HGN GM branch"). A smaller diameter cuff with two or three axially spaced contacts may be used at the HGN GM branch because the nerve fascicles within this branch generally innervate the specific tongue protrusor muscle, but not other muscles. Put another way, the entire HGN GM branch is stimulated with what is predominantly axial vector stimulation. Exemplary nerve cuffs are illustrated and described in U.S. Pat. Pub. Nos. 2018/0318577A1, 2018/0318578A1, 2019/0060646A1 and 2019/0282805, which are incorporated herein by reference in their entirety.

SUMMARY

The present inventors have determined that conventional nerve cuffs are susceptible to improvement. In particular, the present inventors have determined that providing different nerve cuffs for the HGN trunk and HGN GM branch is not cost-effective because each nerve cuff must be separately developed and qualified, and then undergo successful clinical trials and regulatory approvals. Accordingly, the present inventors have determined that it would be desirable to provide a single nerve cuff that is configured in such a manner that it may be selectively placed on, and satisfy the stimulation requirements of, both the HGN trunk and the HGN GM branch.

An electrode lead in accordance with at least one of the present inventions includes an elongate lead body and a nerve cuff. The nerve cuff may include a biologically compatible, elastic, electrically insulative cuff body affixed to the distal end of the lead body, the cuff body being configured to be circumferentially disposed around a nerve, having a pre-set furled state that defines an inner lumen, and being movable to an unfurled state and defining a length and a width in the unfurled state that is greater than the length, first and second relatively wide electrically conductive contacts carried by the cuff body that are spaced from one another in the length direction and that extend in the width direction to such an extent that they extend completely around the cuff body inner lumen when the cuff body is in the pre-set furled shape, a plurality of relatively narrow electrically conductive contacts carried by the cuff body that are spaced from one another in the width direction and are located between the first and second relatively wide electrically conductive contacts, and a plurality of electrical conductors extending through the lead body from at least some of the electrically conductive contacts to the proximal end of the lead body. The present inventions also include systems with an implantable pulse generator or other implantable stimulation device in combination with such an electrode lead.

An electrode lead in accordance with at least one of the present inventions includes an elongate lead body and a nerve cuff. The nerve cuff may include a biologically compatible, elastic, electrically insulative cuff body affixed to the distal end of the lead body, the cuff body being configured to be circumferentially disposed around a nerve, having a pre-set furled state that defines an inner lumen, and being movable to an unfurled state and defining a length and a width in the unfurled state that is greater than the length, a first row of electrically conductive contacts carried by the cuff body that are spaced from one another in the width direction, a second row of electrically conductive contacts carried by the cuff body that are spaced from one another in the width direction, the second row being spaced from the first row in the length direction, a third row of electrically conductive contacts carried by the cuff body that are spaced from one another in the width direction, the third row being located between the first and second rows, and a plurality of electrical conductors extending through the lead body from the electrically conductive contacts to the proximal end of the lead body. The present inventions also include systems with an implantable pulse generator or other implantable stimulation device in combination with such an electrode lead.

An electrode lead in accordance with at least one of the present inventions includes an elongate lead body and a nerve cuff. The nerve cuff may include a T-shaped biologically compatible, elastic, electrically insulative cuff body affixed to the distal end of the lead body, the body being configured to be circumferentially disposed around a nerve, defining a length and a width in the unfurled state that is greater than the length, having a pre-set furled state that defines an inner lumen, and being movable to an unfurled state, a column of electrically conductive contacts carried by the cuff body that are spaced from one another in the length direction, a row of electrically conductive contacts carried by the cuff body that are spaced from one another in the width direction, and a plurality of electrical conductors extending through the lead body from the electrically conductive contacts to the proximal end of the lead body. The present inventions also include systems with an implantable pulse generator or other implantable stimulation device in combination with such an electrode lead. The present inventions also include systems with an implantable pulse generator or other implantable stimulation device in combination with such an electrode lead.

A method in accordance with at least one of the present inventions includes the steps of placing a nerve cuff of an electrode lead on the hypoglossal nerve (HGN) that is configured for placement on either one of the HGN trunk and the branch of the HGN that is responsible for protruding the tongue (HGN GM branch), applying stimulation energy to the HGN trunk with the nerve cuff in instances where the nerve cuff is on the HGN trunk, and applying stimulation energy to the HGN GM branch with the nerve cuff in instances where the nerve cuff is on the HGN GM branch.

BRIEF DESCRIPTION OF THE DRAWINGS

Detailed descriptions of exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 1:
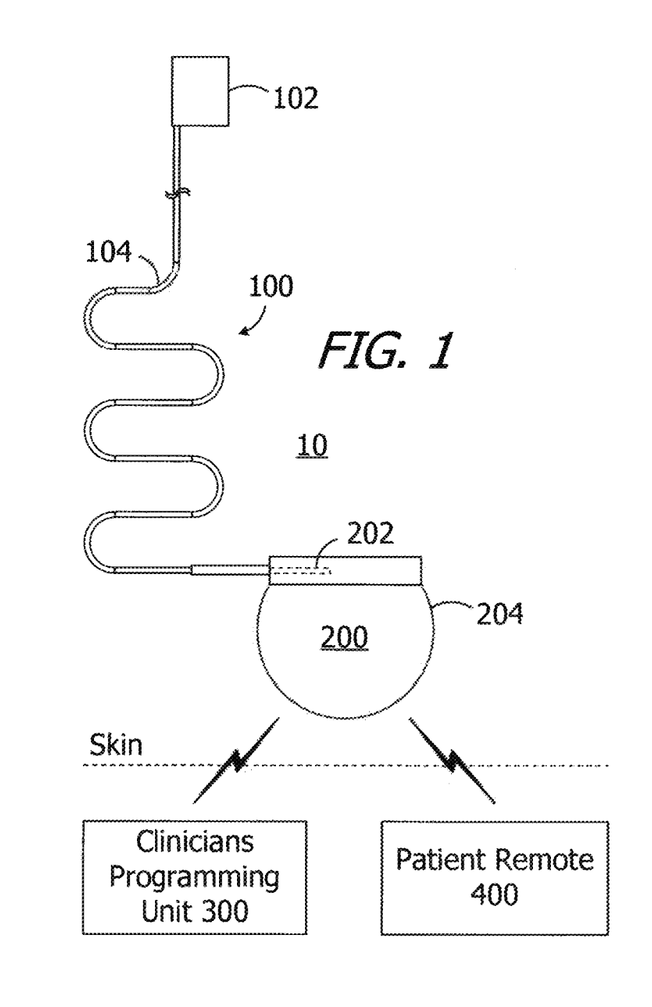
FIG. 1 is a plan view of a stimulation system in accordance with one embodiment of a present invention.
Figure 2:
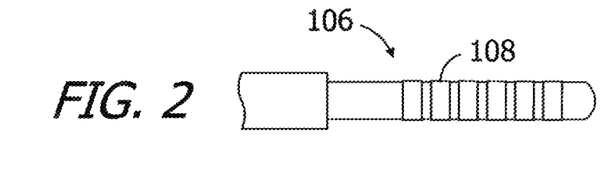
FIG. 2 is a plan view of a portion of the stimulation system illustrated in FIG. 1.

Referring to FIGS. 1 and 2, a stimulation system 10 in accordance with one embodiment of a present invention includes an electrode lead 100 and an implantable stimulator such as the implantable pulse generator ("IPG") 200. A clinician's programming unit 300, a patient remote 400 and an IPG charger (not shown) may also be provided in some instances. The exemplary electrode lead 100 includes a nerve cuff 102 and a lead body 104 that couples the nerve cuff 102 to the IPG 200 by way of lead connector 106, with a plurality contacts 108, on the proximal end of the lead body 104 and a corresponding connector receptacle 202 on the IPG 200. The nerve cuff 102 is configured in such a manner that it may be circumferentially disposed around either the HGN trunk or a HGN branch (e.g., the HGN GM branch) as is discussed below with reference to FIGS. 3 and 4. The lead body 104 may include one or more S-shaped sections in order to provide strain relief (as shown) or may be straight. The S-shaped sections accommodate body movement at the location within the neck where the lead body 104 is implanted, thereby reducing the likelihood that the HGN will be damaged due to unavoidable pulling of the electrode lead 100 that may result from neck movements. The accommodation provided by the S-shaped sections also reduces the likelihood of fatigue damage. Additionally, although the exemplary system 10 includes a single electrode lead 100, other embodiments may include a pair of electrode leads 100 for bilateral HGN stimulation and an IPG (not shown) with two connector receptacles.

Figure 3:
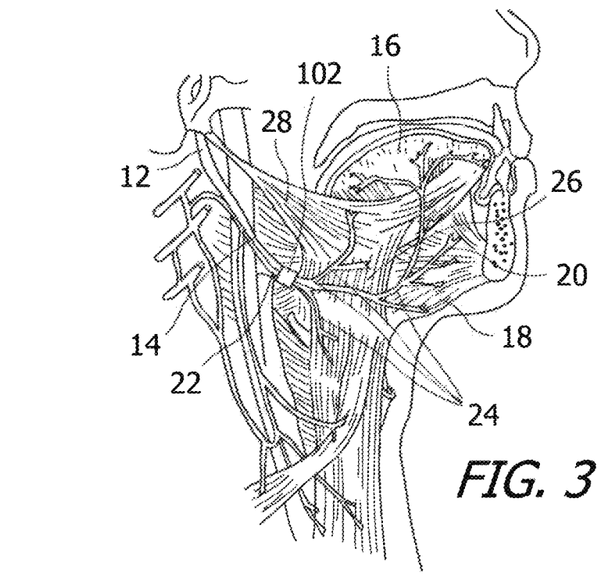
FIG. 3 is a cut-away anatomical drawing of the head and neck area illustrating the muscles that control movement of the tongue, the HGN and its branches that innervate these muscles, and the nerve cuff illustrated in FIG. 1 on the HGN trunk.
Figure 4:
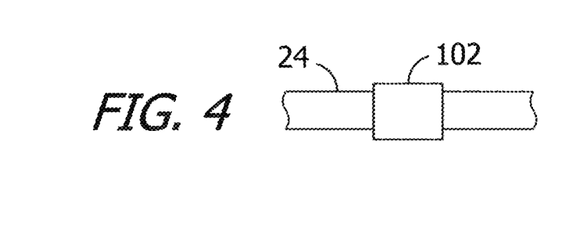
FIG. 4 is a plan view showing the nerve cuff illustrated in FIG. 1 on the HGN GM branch.

Turning to FIG. 3, and as alluded to above, the nerve cuff 102 may be positioned around the trunk 14 of the HGN 12 and used to stimulate the muscles that anteriorly move the tongue 16 and, in particular, the fascicles of the HGN 12 that innervate the tongue protrusor muscles, such as the genioglossus 18 and/or the geniohyoid muscles 20. The nerve cuff 102 is positioned on the HGN trunk 14 at a position 22 proximal to the HGN branches 24. Although there are advantages to implanting the nerve cuff 102 at this proximal position 22, i.e., reduced surgical time and effort as well as reduced risk and trauma to the patient, it introduces the problem of inadvertently stimulating other fascicles of the HGN trunk 14 that innervate muscles in opposition to the genioglossus 18 and/or the geniohyoid muscles 20, i.e., the tongue retractor muscles, e.g., the hyoglossus 26 and styloglossus muscles 28, as well as the intrinsic muscles of the tongue 16. Accordingly, while some clinicians may desire to stimulate the HGN 12 at the HGN trunk 14, others may desire to stimulate the HGN at the GM branch 24. As illustrated in FIG. 4, the same nerve cuff 102 is configured in such a manner that it may be positioned the HGN GM branch 24 instead of the trunk 14.

Figure 5:
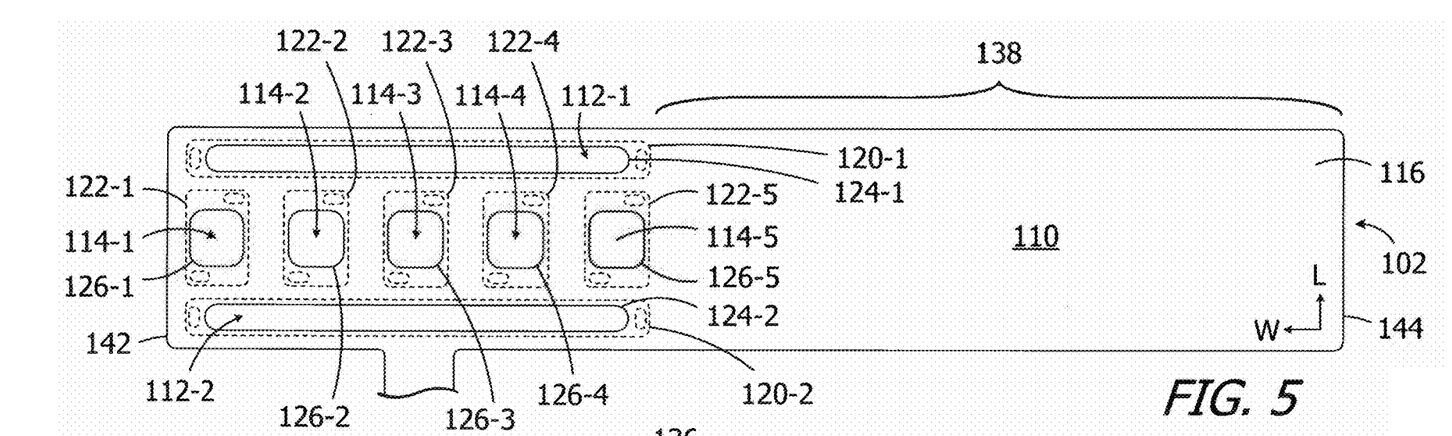
FIG. 5 is a front view of the nerve cuff illustrated in FIG. 1 in an unfurled state.
Figure 6:
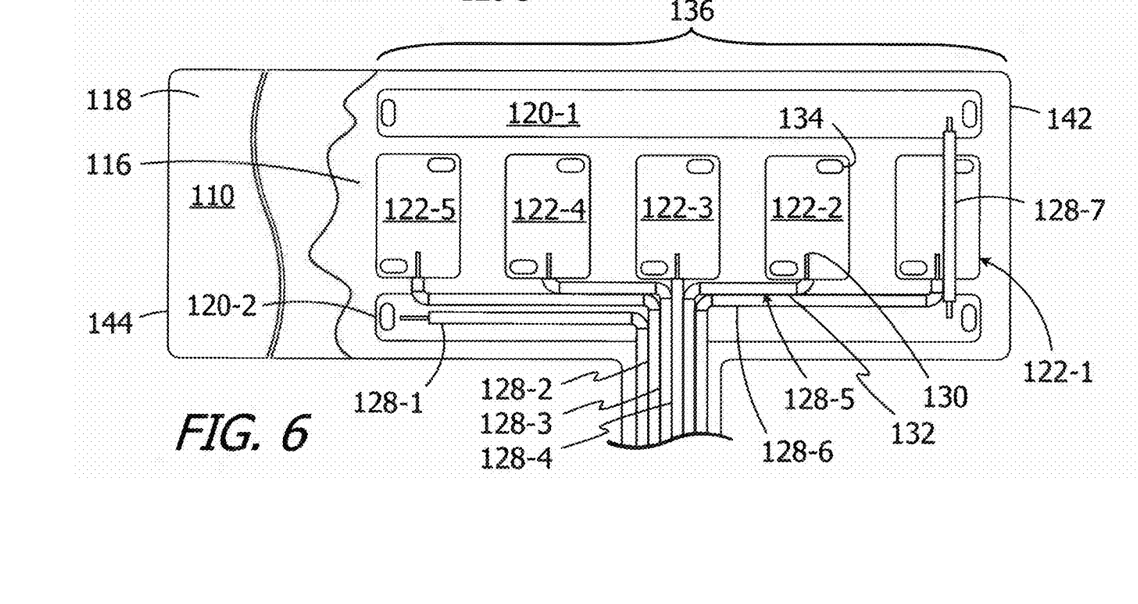
FIG. 6 is a rear, cutaway view of the nerve cuff illustrated in FIG. 1 in an unfurled state.

The exemplary nerve cuff 102 is shown in a flattened, unfurled state in FIGS. 5 and 6 and is shown in various furled states illustrated in FIGS. 7-12 that the nerve cuff will be in when it wraps around an HGN trunk 14 or HGN GM branch 24. In the illustrated implementation, the nerve cuff 102 is pre-set (or "pre-shaped") to the furled (or "curled") state illustrated in FIGS. 7 and 8, and an external force may be used to partially or completely unfurl the nerve cuff 102. The nerve cuff 102 will return to the pre-shaped furled state when the force is removed and, as discussed below, may assume one of the furled states illustrated in FIGS. 7-12 depending on the size of the HGN trunk or HGN branch that the nerve cuff 102 is placed around. Various examples of nerve cuffs that are capable of assuming different sizes are disclosed in aforementioned U.S. Pat. Pub. No. 2019/0060646A1.

Referring first to FIGS. 5 and 6, the nerve cuff 102 includes a cuff body 110 that defines a length and a width that is greater than the length, first and second relatively wide electrically conductive contacts (or "relatively wide contacts") 112-1 and 112-2 on the cuff body 110 that extend in the width direction and are spaced from one another in the length direction and a plurality of relatively narrow electrically conductive contacts (or "relatively narrow contacts") 114. Although the number may increase or decrease in the context of other nerve applications, at least five relatively narrow electrically conductive contacts (or "relatively narrow contacts") 114 may be spaced from one another in the width direction and are located between the first and second relatively wide contacts 112-1 and 112-2, and are five relatively narrow contacts 114-1 to 114-5 in the illustrated embodiment. As used herein, "relatively wide" structures are structures that are longer in the width direction than structures that are referred to as "relatively narrow" and "relatively narrow" structures are structures that are shorter in the width direction than structures that are referred to as "relatively wide." In the implementation illustrated in FIGS. 5 and 6, the relatively narrow contacts 114-1 to 114-5 are centered relative to the relatively wide contacts 112-1 and 112-2 and are aligned with one another in the length direction. In other implementations, the relatively narrow contacts may be non-centered relative to the relatively wide contacts 112-1 and 112-2 and/or offset from one another in the length direction. With respect to shape, and although the present inventions are not so limited, the relatively wide contacts 112-1 and 112-2 are in the shape of rectangles with semi-circular ends, while the relatively narrow contacts 114-1 to 114-5 are squares with rounded corners. Other exemplary shapes include, but are not limited to, circles, ellipses, squares, and rectangles.

The contacts 112-1 to 114-5 may be of any suitable construction. In the illustrated implementation, the cuff body 110 includes a front layer 116 that will face the HGN trunk or branch and a rear layer 118 that will face away from the HGN trunk or branch. First and second relatively wide conductive members 120-1 and 120-2 and five relatively narrow conductive members 122-1 to 122-5 are located between the front layer 116 and rear layer 118. The relatively wide conductive members 120-1 and 120-2 are exposed by way of relatively wide openings 124-1 and 124-2 in the cuff body front layer 116, while the relatively narrow conductive members 122-1 to 122-5 are exposed by way of relative narrow openings 126-1 to 126-5 in the cuff body front layer 116. The openings 124-1 to 126-5 extend from the outer surface of the front layer 116 to the associated conductive members 120-1 to 122-5, and the exposed portions of the conductive members 120-1 to 122-5 define the contacts 112-1 to 114-5. The conductive members 120-1 and 122-5 may also include apertures 134 that, in conjunction with the material that forms the cuff body layers 116 and 118 and enters the apertures, anchor the conductive members in their intended locations.

The contacts 112-1 to 114-5 in the illustrated embodiment may be electrically connected to the plurality contacts 108 on the lead connector 106 (FIG. 2) by wires 128-1 to 128-6 that extend through the lead body 104 as well as by a wire 128-7 that connects contact 112-1 to contact 112-2. The contacts 112-1 and 112-2 may also be separately connected to respective contacts on the lead connector 106 in other implementations. Each wire 128-1 to 128-7 includes a conductor 130 and an insulator 132. The conductors 130 may be connected to the rear side of the conductive members 120-1 to 122-5 by welding or other suitable processes.

Figure 6A:
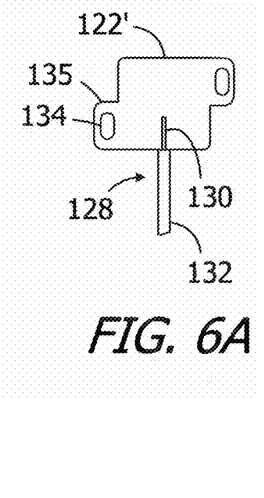
FIG. 6A is a rear view of a conductive member in accordance with one embodiment of a present invention.

Although the exemplary relatively narrow conductive members 122-1 to 122-5 are generally rectangular in shape and the apertures 134 are located in two of the corners of the rectangular conductive members in the exemplary nerve cuff 102, the present relatively narrow conductive members are not limited to particular shapes and aperture locations. By way of example, but not limitation, the exemplary relatively narrow conductive member 122' illustrated in FIG. 6A are generally square in shape and the apertures 134 are located on tabs 135 that extend in the width direction. The conductive members 122', which provide additional distance between the apertures 134 and the conductor connection location, may form part of any of the exemplary nerve cuffs described herein.

The cuff body 110 in the exemplary implementation illustrated in FIGS. 5 and 6 includes a stimulation region 136 and a compression region 138. The contacts 112-1 to 114-5 are located within the stimulation region 136. There are no contacts located within the compression region 138. The compression region 138 wraps around at least a portion of the stimulation region 136 when the nerve cuff 102 is in the pre-shaped furled state and the slightly larger, expanded and less tightly furled states described below with reference to FIGS. 7-12, thereby resisting (but not preventing) expansion of the stimulation region and improving the electrical connection between the contacts 112-1 to 114-5 and the HGN.

Figure 7:
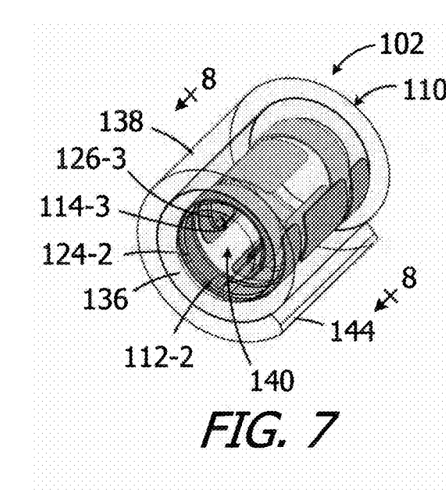
FIG. 7 is a perspective view of the nerve cuff illustrated in FIG. 1 in a pre-shaped furled state.
Figure 8:
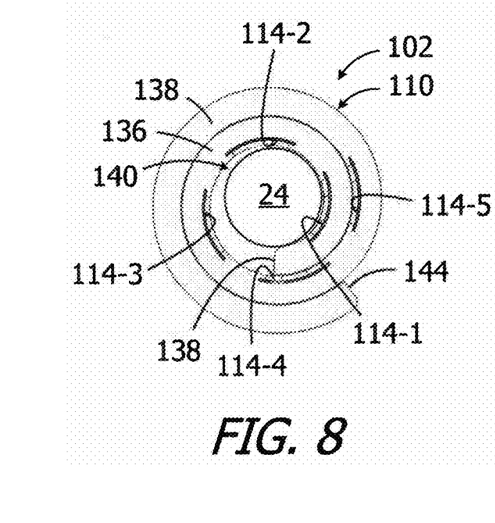
FIG. 8 is a section view taken along line 8-8 in FIG. 7 with a HGN branch added.
Figure 9:
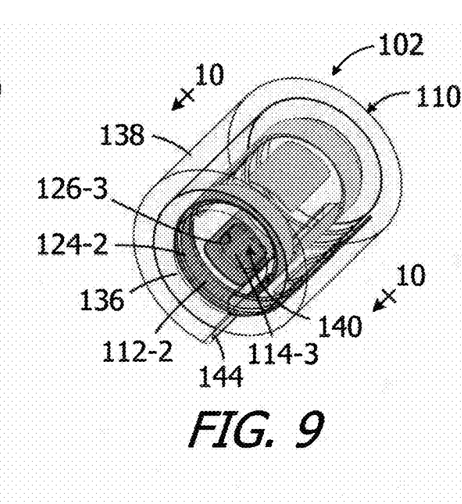
FIG. 9 is a perspective view of the nerve cuff illustrated in FIG. 1 in an expanded and less tightly furled state.
Figure 10:
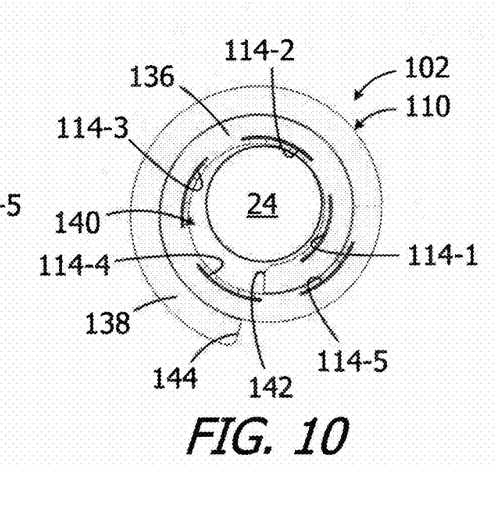
FIG. 10 is a section view taken along line 10-10 in FIG. 9 with a HGN branch added.
Figure 11:
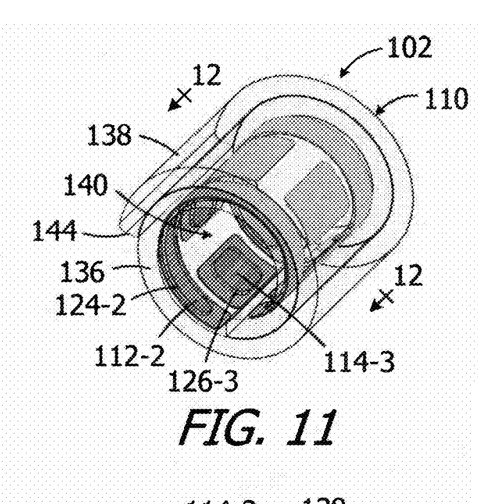
FIG. 11 is a perspective view of the nerve cuff illustrated in FIG. 1 in an expanded and less tightly furled state.
Figure 12:
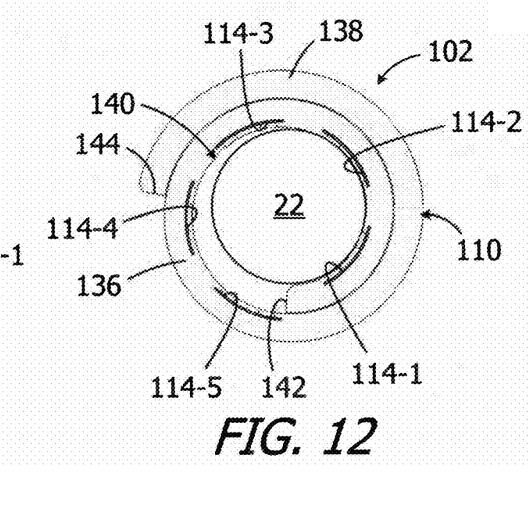
FIG. 12 is a section view taken along line 12-12 in FIG. 11 with a HGN trunk added.

The exemplary cuff body 110 may be formed from any suitable material. Such materials may be biologically compatible, electrically insulative, elastic and capable of functioning in the manner described herein. By way of example, but not limitation, suitable cuff body materials include silicone, polyurethane and liquid crystal polymers that are pliable enough to allow a clinician to unfurl the cuff body 110 (and nerve cuff 102) and place the nerve cuff around the HGN trunk (or HGN GM branch). The exemplary materials should also be resilient enough to cause the nerve cuff return to the pre-shaped furled state illustrated in FIGS. 7 and 8 when the force is removed, yet flexible enough to allow the cuff body 110 (and nerve cuff 102) to instead assume the slightly larger, expanded and less tightly furled states illustrated in FIGS. 9-12. To that end, the furled cuff body 110 defines an inner lumen 140, in which the nerve will be located after the nerve cuff 102 wraps around the nerve, as well as lateral ends 142 and 144 that are respectively associated with the stimulation region 136 and the compression region 138. Comparing the state illustrated in FIGS. 9 and 10 to that state illustrated in FIGS. 7 and 8, the inner lumen 140 is slightly larger and the lateral end 144 is offset around the perimeter of the nerve cuff 102. Similarly, comparing the state illustrated in FIGS. 11 and 12 to that state illustrated in FIGS. 9 and 10, the inner lumen 140 is slightly larger and the lateral end 144 is offset around the perimeter of the nerve cuff 102. For example, the inner lumen 140 in FIGS. 7 and 8 is sized to accommodate an HGN structure that has a diameter of about 2.5 mm (e.g., the HGN GM branch 24), the inner lumen 140 in FIGS. 9 and 10 is sized to accommodate an HGN structure that has a diameter of about 3.0 mm (e.g., the HGN GM branch 24 in a swollen state), and the inner lumen 140 in FIGS. 11 and 12 is sized to accommodate an HGN structure that has a diameter of about 4.0 mm (e.g., the HGN trunk 22). The ability to assume slightly larger, expanded and less tightly furled states, in addition to the smaller fully furled state, allows the same nerve cuff 102 to accommodate ether of the larger HGN trunk 14 or an smaller HGN branch 24. The ability to assume slightly larger, expanded furled states also allows the nerve cuff to accommodate nerve swelling that may occur post-surgery and to self-adjust to a smaller state when the swelling subsides.

It should also be noted here that the relatively wide contacts 112-1 and 112-2 are sized such that they extend completely around the inner lumen 140, i.e., 360° or more around the longitudinal axis of the inner lumen, when the cuff body 110 is in the fully furled state illustrated in FIGS. 7 and 8 that accommodates an HGN structure having a diameter of about 2.5 mm. Viewed as a group, the relatively narrow contacts 114-1 to 114-5 also extend completely around the inner lumen 140 when the when the cuff body 110 is in the fully furled state illustrated in FIGS. 7 and 8. The relatively wide contacts 112-1 and 112-2 also extend substantially around the inner lumen 140, i.e., at least 288° or more around the longitudinal axis of the inner lumen, when the cuff body 110 is in the expanded and less tightly furled state illustrated in FIGS. 11 and 12 that accommodates an HGN structure having a diameter of about 4.0 mm. Viewed as a group, the relatively narrow contacts 114-1 to 114-5 also extend substantially around the inner lumen 140 when the when the cuff body 110 is in the expanded and less tightly furled state illustrated in FIGS. 11 and 12.

Figure 13:
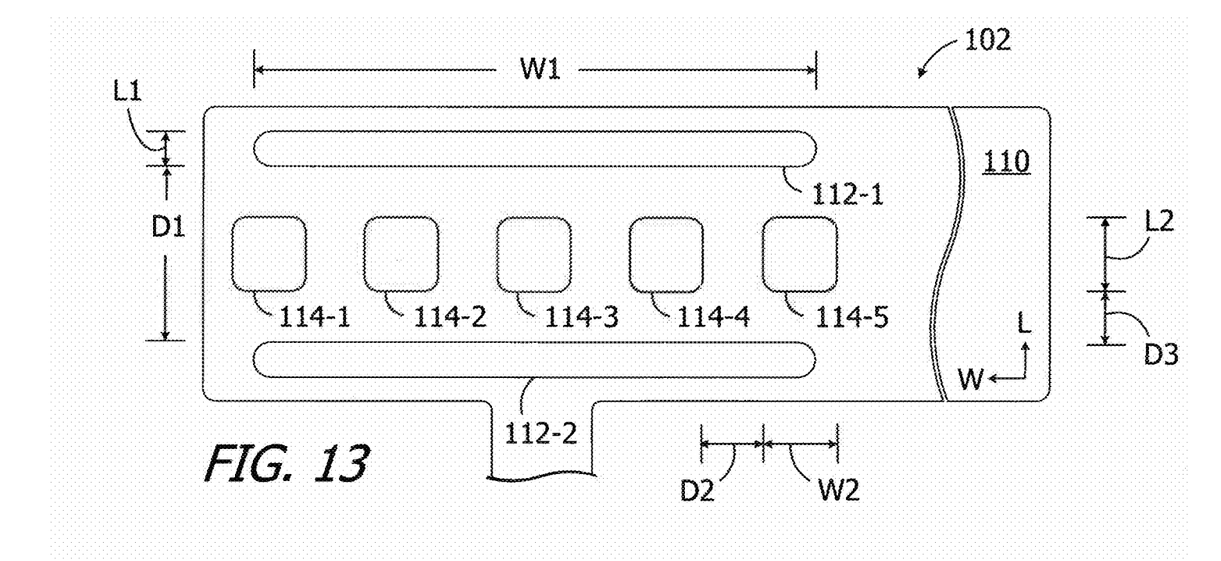
FIG. 13 is a front view of the nerve cuff illustrated in FIG. 1 in an unfurled state.

The dimensions of the present nerve cuffs, including the various elements thereof, may by any dimensions that result in the nerve cuffs functioning as intended. With respect to the dimensions of the cuff body 110 of the exemplary nerve cuff 102, the cuff body is about 1.35 inches wide and about 0.26 inches long. As used herein in the context of dimensions, the word "about" means±10-20%, The width of the stimulation region 136 is about 0.60 inches, while the width of the compression region 138 is about 0.75 inches. The relatively wide contacts 112-1 and 112-2 are same size, and the relatively narrow contacts 114-1 to 114-5 are the same size, in the illustrated implementation. In other implementations, the relatively wide contacts 112-1 and 112-2 may be different sizes and/or the relatively narrow contacts 114-1 to 114-5 may be different sizes. Referring to FIG. 13, the width W1 of the relatively wide contacts 112-1 and 112-2 is about 0.53 inches, the length L1 is about 0.3 inches, and the distance D1 between the relatively wide contacts 112-1 and 112-2 is about 0.14 inches. The width W2 of the relatively narrow contacts 114-1 to 114-5 is about 0.5 inches, the length L2 is about 0.06 inches and the distance D2 between the relatively narrow contacts 114-1 to 114-5 is about 0.06 inches. The distance D2 may also be increased or decreased as desired to accomplish various stimulation objectives. The distance D3 between the relatively narrow contacts 114-1 to 114-5 and the relatively wide contacts 112-1 and 112-2 is about 0.06 inches.

Figure 14:
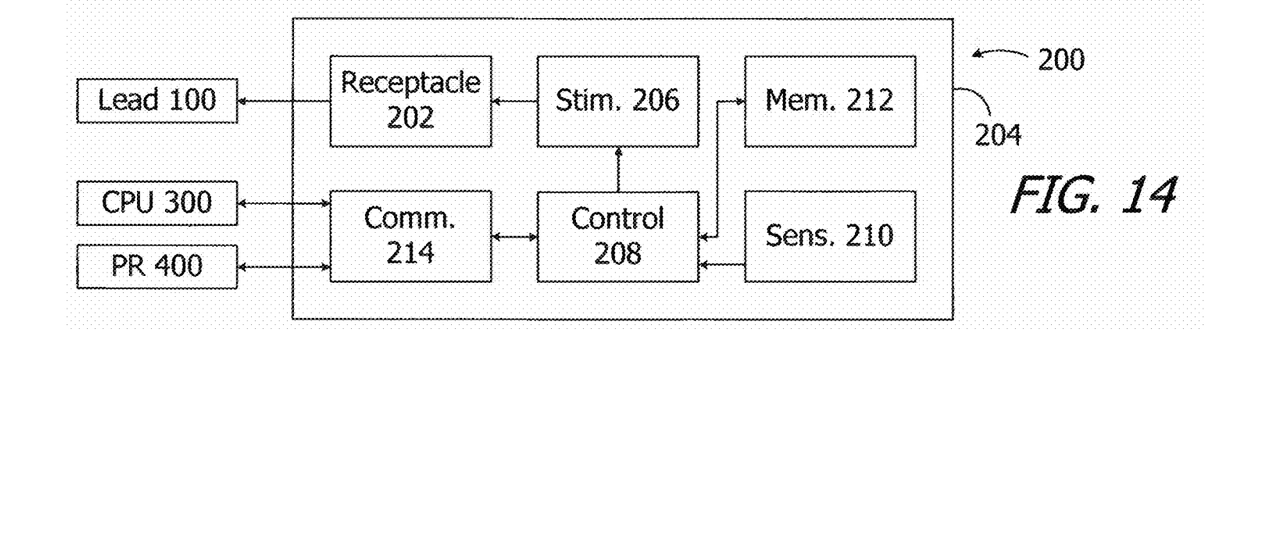
FIG. 14 is a block diagram of the stimulation system illustrated in FIG. 1.

Turning to FIG. 14, the exemplary IPG 200 includes the aforementioned receptacle 202, a hermetically sealed outer case 204, and various circuitry (e.g., stimulation circuitry 206, control circuitry 208, sensing circuitry 210, memory 212, and communication circuitry 214) that is located within the outer case 204. The outer case 204 may be formed from an electrically conductive, biocompatible material such as titanium. The stimulation circuitry 206, which is coupled to the contacts 112-1 to 114-5 by way of the connector 106, receptacle 202 and wires 128-1 to 128-7, is configured to deliver stimulation energy to the HGN. The control circuitry 208 controls when and for how long the stimulation circuitry 206 applies stimulation, the intensity of the stimulation, the mode of stimulation (i.e., monopolar, bipolar or tripolar), and the particular contacts that are used in the stimulation. In the monopolar stimulation, at least a portion of the outer case 204 functions as a return electrode in the electrical circuit that also includes one or more of the contacts 112-1 to 114-5. In bipolar stimulation, the outer case 204 is not part of the electrical circuit and current instead flows from one of the contacts 112-1 to 114-5 to one of the other contacts 112-1 to 114-5. In tripolar stimulation, the outer case 204 is not part of the electrical circuit and current flows from one or more of the contacts 112-1 to 114-5 to more than one of the other contacts 112-1 to 114-5. The contacts that the current flows to form part of the return path for the stimulation energy, as do the associated wires connected thereto. The stimulation may also be predominantly axial vector stimulation, predominantly radial vector stimulation, or a hybrid of axial vector and radial vector.

It should also be noted here that in most instances, contacts that are entirely separated from (and electrically disconnected from) the associated nerve by the cuff body will not be used by the IPG for current transmission and return. For example, when the exemplary nerve cuff 102 is in less lightly furled state illustrated in FIG. 10, the contact 114-5 is entirely separated from the GM branch 24 by the electrically non-conductive cuff body 110 and will not be used for current transmission or return. Such contacts may be identified by, for example, measuring the impedance at each contact.

The sensing circuitry 210 in the illustrated embodiment may be connected to one or more sensors (not shown) that are contained within the outer case 204. Alternatively, or in addition, the sensors may be affixed to the exterior of the outer case 204 or positioned at a remote site within the body and coupled to the IPG 200 with a connecting lead. The sensing circuitry 210 can detect physiological artifacts that are caused by respiration (e.g., motion or ribcage movement), which are proxies for respiratory phases, such as inspiration and expiration or, if no movement occurs, to indicate when breathing stops. Suitable sensors include, but are not limited to, inertial sensors, bioimpedance sensors, pressure sensors, gyroscopes, ECG electrodes, temperature sensors, GPS sensors, and combinations thereof. The memory 212 stores data gathered by the sensing circuitry 210, programming instructions and stimulation parameters. The control circuitry 208 analyzes the sensed data to determine when stimulation should be delivered. The communication circuitry 214 is configured to wirelessly communicates with the clinician's programming unit 300 and patient remote 400 using radio frequency signals.

The control circuitry 208 may apply stimulation energy to either the HGN truck or an HGN branch (e.g. the HGN GM branch) in various stimulation methodologies by way of the cuff 102 when the patient is in the inspiratory phase of respiration, and other conditions for stimulation are met, thereby causing anterior displacement of the tongue to keep the upper airway unobstructed. The control circuitry 208 causes the stimulation circuitry 206 to apply stimulation in the form of a train of stimulation pulses during these inspiratory phases of the respiratory cycle (or slightly before the inspiration and ending at the end of inspiration) and not the remainder of the respiration cycle. The train of stimulus pulses may be set to a constant time duration or may change dynamically based on a predictive algorithm that determines the duration of the inspiratory phase of the respiratory cycle.

Figure 15A:
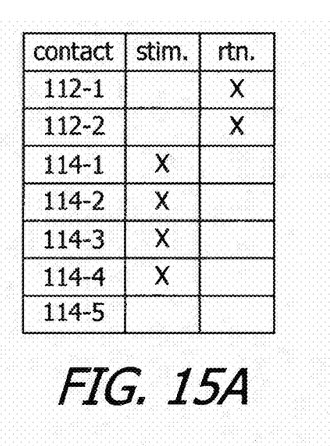
FIG. 15A is a table showing a stimulation methodology in accordance with one embodiment of a present invention.
Figure 15B:
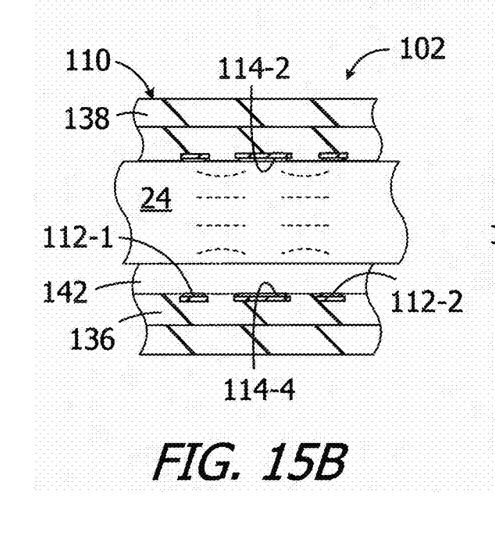
FIG. 15B is a section view showing stimulation of the HGN GM branch using the methodology illustrated in FIG. 15A.

One exemplary stimulation methodology is illustrated in FIGS. 15A and 15B. Here, the nerve cuff 102 is positioned on an HGN branch 24 (such as the HGN GM branch) and is in the pre-shaped furled state illustrated in FIGS. 4, 7 and 8. The IPG 200 supplies stimulation energy to each of the relatively narrow contacts 114-1 to 114-4 and the relatively wide contacts 112-1 and 112-2 form part of the return path for the stimulation energy. In other words, the relatively narrow contacts 114-1 to 114-4 function as cathodes and the relatively wide contacts 112-1 and 112-2 function as anodes. The contacts 112-1 to 114-4 encircle the HGN branch 24 (such as the HGN GM branch) and the stimulation current has a predominantly axial vector along the HGN branch and, as a result, the entire HGN branch is stimulated.

Figure 15C:
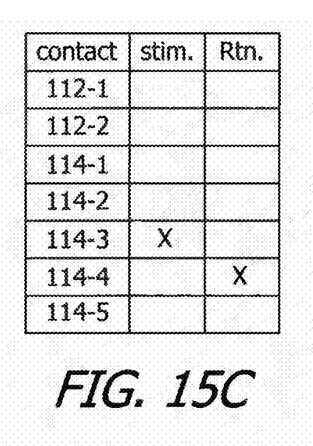
FIG. 15C is a table showing a stimulation methodology in accordance with one embodiment of a present invention.
Figures 15D, 15F:
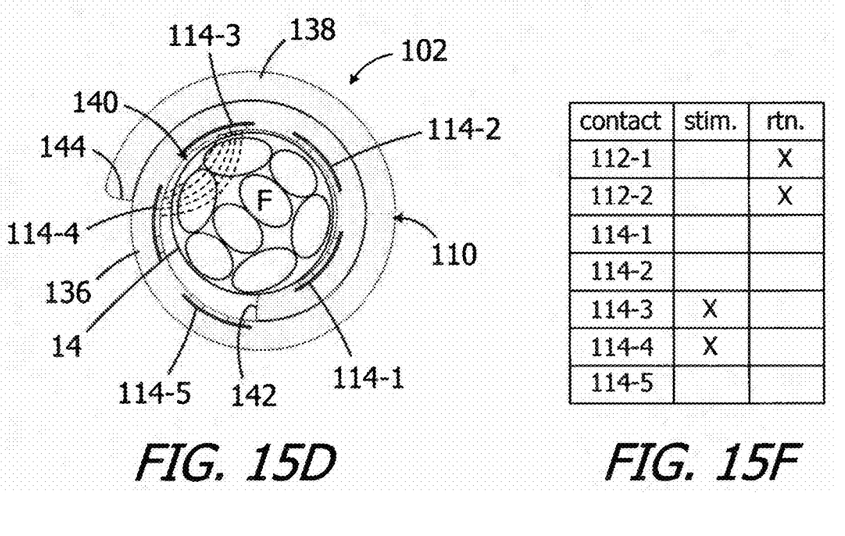
FIG. 15D is a section view showing stimulation of the HGN trunk using the methodology illustrated in FIG. 15C.
FIG. 15F is a table showing a stimulation methodology in accordance with one embodiment of a present invention.

Another exemplary stimulation methodology is illustrated in FIGS. 15C and 15D. Here, the nerve cuff 102 is positioned on the HGN trunk 14 and is in the larger, expanded and less tightly furled state illustrated in FIGS. 11 and 12. So positioned, the nerve cuff 102 may be used to selectively stimulate nerve fascicles F which innervate muscles that extend the tongue, while avoiding other nerve fascicles. For example, the IPG 200 may supply stimulation energy to relatively narrow contact 114-3, and use the relatively narrow contact 114-4 to form the return path for the stimulation energy. In other words, the relatively narrow contact 114-3 functions as a cathode and the relatively narrow contact 114-4 functions as an anode. The remaining contacts (i.e., contacts 112-1, 112-2, 114-1, 114-2 and 114-5) are not used to supply stimulation energy to the HGN trunk 14. Nor do the remaining contacts form part of the return path for the stimulation energy. As a result, the IPG 200 is able to use the nerve cuff 102 to steer the stimulation current to such an extent that stimulation is effective over only the desired section of the HGN trunk 14, thereby stimulating the desired fascicle(s) in the HGN trunk, while not providing enough stimulation to excite the other fascicles. It should also be noted that stimulation current applied only between two or more of the relatively narrow contacts 114-1 to 114-5 has a predominantly radial vector.

Figure 15E:
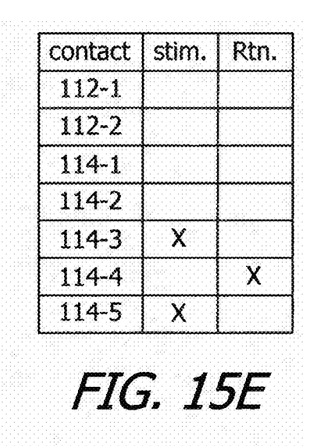
FIG. 15E is a table showing a stimulation methodology in accordance with one embodiment of a present invention.

Another exemplary stimulation methodology is illustrated in FIG. 15E. The methodology is substantially similar to that illustrated in FIGS. 15C and 15D, and may be used to stimulate particular fascicles within the HGN trunk 14. Here, however, the IPG 200 supplies stimulation energy to relatively narrow contacts 114-3 and 114-5, while relatively narrow contact 114-4 forms part of the return path for the stimulation energy. In other words, the relatively narrow contacts 114-3 and 114-5 function as cathodes and the relatively narrow contact 114-4 functions as an anode. The remaining contacts (i.e., contacts 112-1, 112-2, 114-1, 114-2 and 114-5) are not used to supply stimulation energy to the HGN trunk 14. Nor do the remaining contacts form part of the return path for the stimulation energy. Applying stimulation energy in this way results in a greater number of fascicles being stimulated, while also not providing enough stimulation to excite the remaining fascicles. The number of relatively narrow contacts used as anodes or cathodes may also be increased or decreased to suit particular stimulation objectives. It should also be noted that the stimulation current has a predominantly radial vector.

Hybrid stimulation methodologies, with both axial and radial vectors, may be employed. Here, one or more of the relatively wide contacts 112-1 and 112-2 may be used in conjunction with one or more the relatively narrow contacts 114-1 to 114-5. The nerve cuff will be a nerve cuff where the relatively wide contacts 112-1 and 112-2 are individually connected to the lead connector 106 in those instances where only one relatively wide contact is employed. In the exemplary stimulation methodology illustrated in FIG. 15F, which may be used to stimulate particular fascicles within the HGN trunk 14, the IPG 200 supplies stimulation energy to relatively narrow contacts 114-3 and 114-4, while relatively wide contacts 112-1 and 112-2 form part of the return path for the stimulation energy. In other words, the relatively narrow contacts 114-3 and 114-4 function as cathodes and the relatively wide contacts 112-1 and 112-2 functions as anodes. The remaining contacts (i.e., contacts 114-1, 114-2 and 114-5) are not used to supply stimulation energy to the HGN trunk 14. Nor do the remaining contacts form part of the return path for the stimulation energy.

Figure 15G:
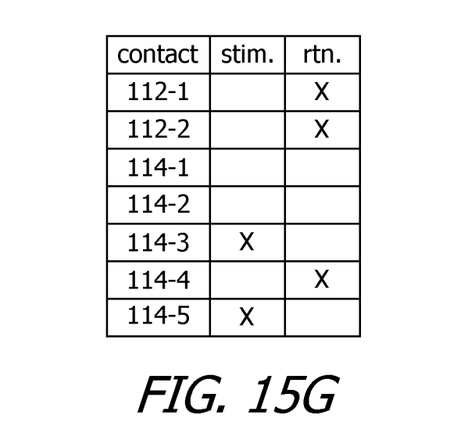
FIG. 15G is a table showing a stimulation methodology in accordance with one embodiment of a present invention.

Another exemplary stimulation methodology is illustrated in FIG. 15G. The methodology is similar to that illustrated in FIG. 15F. Here, however, the IPG 200 supplies stimulation energy to relatively narrow contacts 114-3 and 114-5, while relatively wide contacts 112-1 and 112-2 and relatively narrow contact 114-4 form part of the return path for the stimulation energy. In other words, the relatively narrow contacts 114-3 and 114-5 function as cathodes and the relatively wide, contacts 112-1 and 112-2 and relatively narrow contact 114-4 function as anodes. The remaining contacts (i.e., contacts 114-1 and 114-2) are not used to supply stimulation energy to the HGN trunk 14. Nor do the remaining contacts form part of the return path for the stimulation energy. Applying stimulation energy in this way results in stimulation with axial and radials vectors that reaches fascicles deeper in the HGN trunk.

Figure 16:
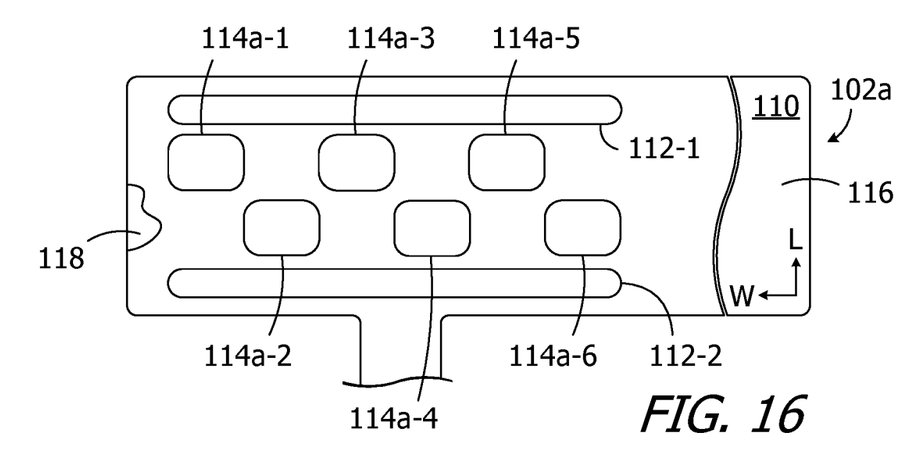
FIG. 16 is a front view of a nerve cuff in accordance with one embodiment of a present invention in an unfurled state.

Another exemplary nerve cuff is generally represented by reference numeral 102a in FIG. 16. Nerve cuff 102a is substantially similar to nerve cuff 102 and similar elements are represented by similar reference numerals. For example, the nerve cuff 102a may form part of an electrode lead 100 that may be connected to the IPG 200, or other suitable device, and employed in stimulation methodologies such as those described above. The nerve cuff 102a includes a cuff body 110 with a front layer 116, a rear layer 118, first and second relatively wide conductive members that are exposed by way of relatively wide openings in the front layer 116 to define relatively wide contacts 112-1 and 112-2, and a plurality of relatively narrow conductive members that are exposed by way of relatively narrow openings front layer 116 to define relatively narrow contacts that are located between the relatively wide contacts 112-1 and 112-2. Here, however, the six relatively narrow contacts 114a-1 to 114a-6 are not centered relative to the relatively wide contacts 112-1 and 112-2 and are not all aligned with one another in the length direction. Relatively narrow contact 114a-1, 114a-3 and 114a-5 are closer to the relatively wide contact 112-1 and are aligned with one another in the length direction, while relatively narrow contact 114a-2, 114a-4 and 114a-6 are closer to the relatively wide contact 112-2 and are aligned with one another in the length direction.

In the illustrated implementation, the distance in the length direction between the relatively wide contact 112-1 and the relatively narrow contacts 114a-1, 114a-3 and 114a-5 is equal to the distance in the length direction between the relatively wide contact 112-2 and the relatively narrow contacts 114a-2, 114a-4 and 114a-6 which is, in turn, equal to the distance in the length direction between the relatively narrow contacts 114a-1, 114a-3 and 114a-5 and the relatively narrow contacts 114a-2, 114a-4 and 114a-6. Also, the ends of adjacent relatively narrow contacts 114a are aligned with one another in the width direction. Such a contact arrangement may in some circumstances facilitate, as compared to the arrangement illustrated in FIGS. 5-13, greater fascicle stimulation specificity by placing the corners of adjacent relatively narrow contacts closer to one another without adversely affecting the flexibility of the nerve cuff.

Figure 17:
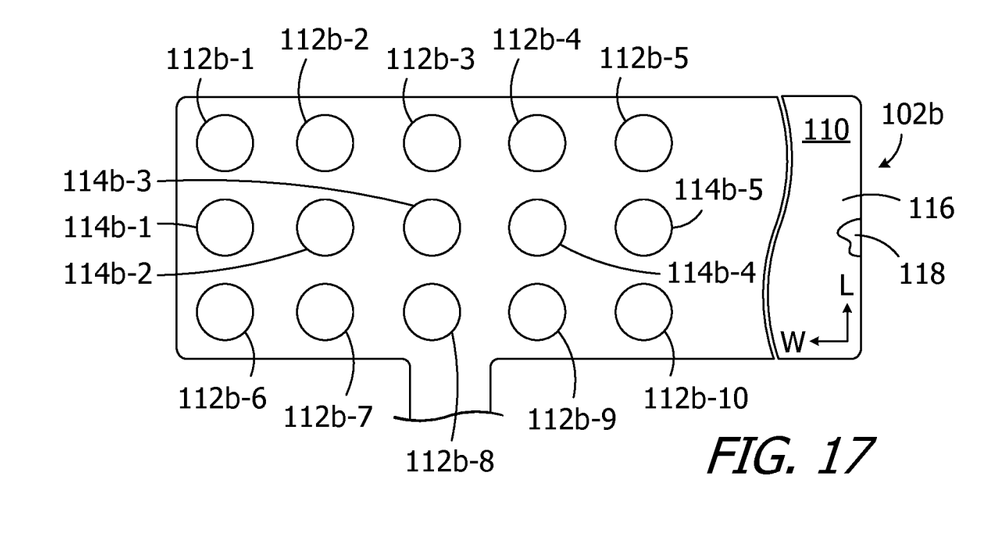
FIG. 17 is a front view of a nerve cuff in accordance with one embodiment of a present invention in an unfurled state.
Figure 17A:
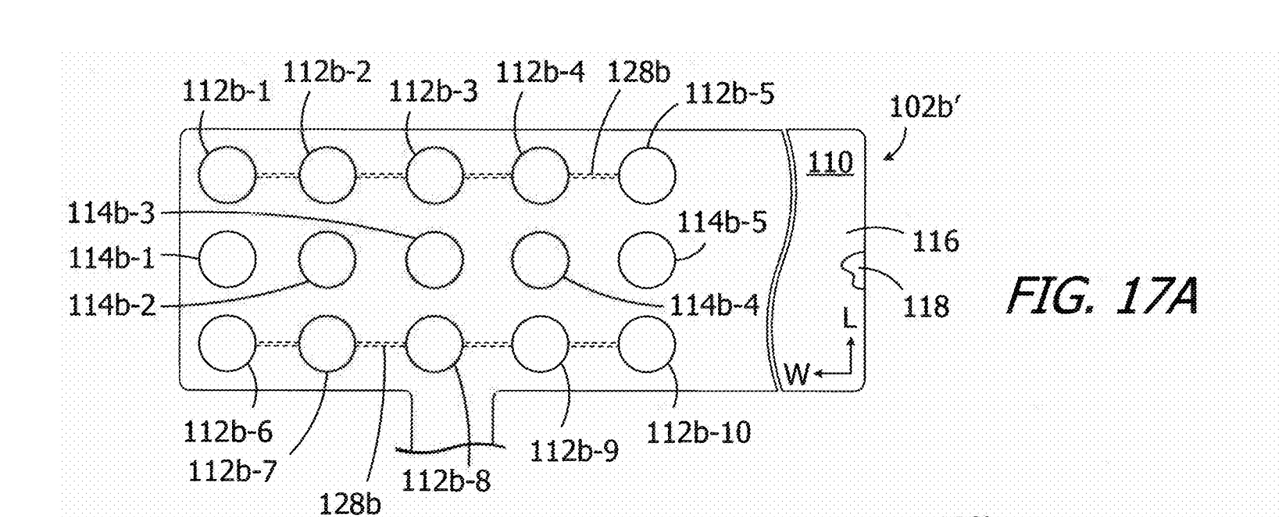
FIG. 17A is a front view of a nerve cuff in accordance with one embodiment of a present invention in an unfurled state.

Turning to the FIG. 17, exemplary nerve cuff 102b is generally is substantially similar to nerve cuff 102 and similar elements are represented by similar reference numerals. For example, the nerve cuff 102b includes a cuff body 110 with a front layer 116, a rear layer 118, and a plurality of contacts that are formed by conductive members and openings in the front layer 116. Here, however, there are three rows of contacts that extend in the width direction, i.e., the row consisting of contacts 112b-1 to 112b-5, the row consisting of contacts 112b-6 to 112b-10 and the row therebetween consisting of contacts 114b-1 to 114b-5. Although the contacts within each row are aligned in the width direction, they may be offset in other implementations, and although contacts from each row from are aligned in the length direction, they may be offset in other implementations. Additionally, the contacts 112b-1 to 112b-10 and 114b-1 to 114b-5 may each be connected to the lead connector by its own respective wire (note wires 128-1 to 128-6 in FIG. 6) so that each contact can be separately controlled by the IPG 200. In other instances, two or more of the contacts may be connected to one another by a wire and commonly controlled by a single wire that extends to the connector 106. For example, in some instances such as the nerve cuff 102b' illustrated in FIG. 17A, a plurality of wires 128b may be used to connect contacts 112b-1 to 112b-5 to one another in series and/or a plurality of wires 128b may be used to connect contacts 112b-6 to 112b-10 to one another in series. In other instances such as the nerve cuff 102b" illustrated in FIG. 17B, subsets of the contacts 112b-1 to 112b-5 (e.g., contacts 112b-1 and 112b-2) may be connected to one another in series with wires 128b and/or subsets of the contacts 112b-6 to 112b-10 (e.g., contacts 112b-7 and 112b-8) may be connected to one another in series with wires 128b.

Figure 17B:
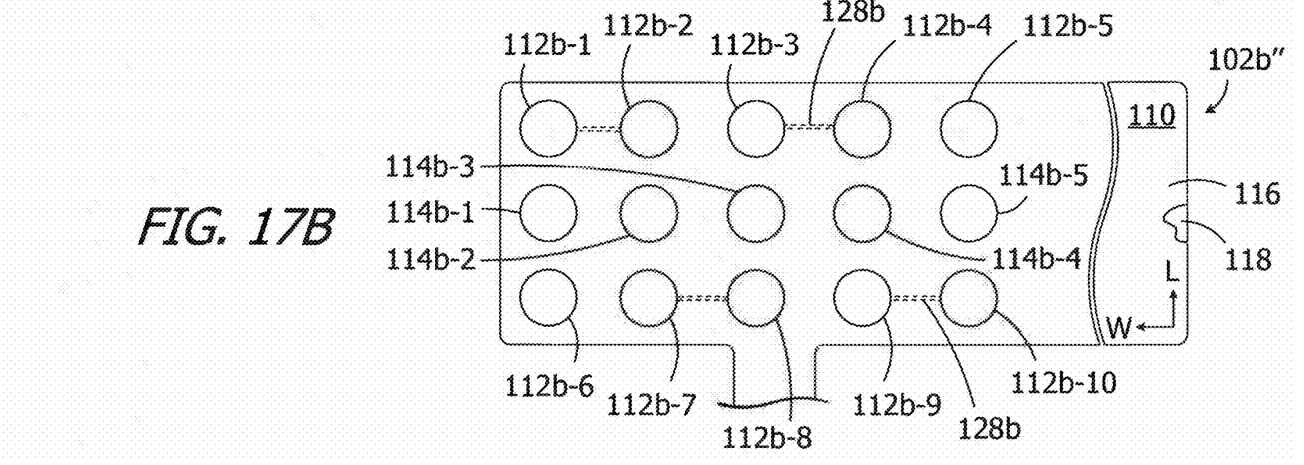
FIG. 17B is a front view of a nerve cuff in accordance with one embodiment of a present invention in an unfurled state.
Figure 18:
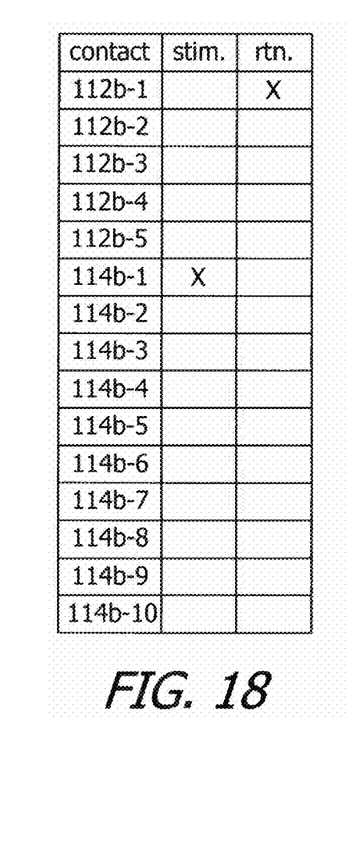
FIG. 18 is a table showing a stimulation methodology in accordance with one embodiment of a present invention.
Figure 18A:
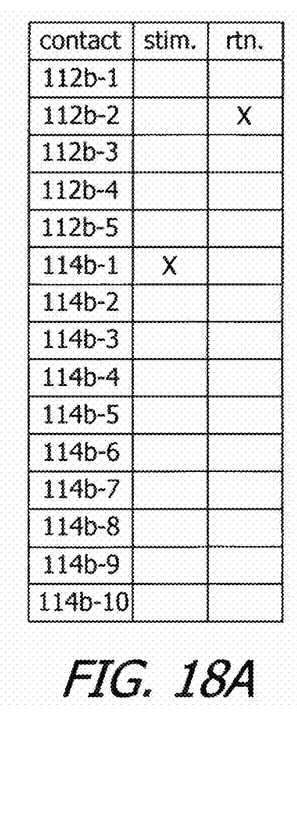
FIG. 18A is a table showing a stimulation methodology in accordance with one embodiment of a present invention.
Figure 18B:
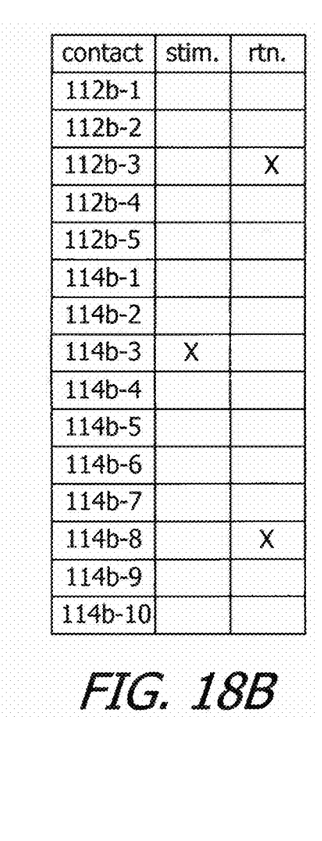
FIG. 18B is a table showing a stimulation methodology in accordance with one embodiment of a present invention.

The exemplary nerve cuff 102b illustrated in FIGS. 17-17B may be employed in a stimulation methodologies similar to that illustrated in FIG. 15k Here, the IPG 200 may supply stimulation energy to some or all of the contacts 114b-1 to 114b-5, while some or all of the contacts 112b-1 to 112-b10 form part of the return path for the stimulation energy. In other instances, stimulation energy may be supplied to some or all of contacts 112b-1 to 112b10, while some or all of the contacts 114b-1 to 114b-5 may form part of the return path. Separating the relatively wide contacts 112 into respective pluralities of spaced contacts 112b, that can be selectively employed, facilitates greater charge density in the desired location. This may be especially useful when the nerve cuff 102b is on the HGN GM branch. The nerve cuff 102b may be employed in, for example, the stimulation methodology illustrated in FIG. 18. Here, the IPG 200 supplies stimulation energy to contact 114b-1, while contact 112b-1 forms part of the return path for the stimulation energy, which results in predominantly axial vector stimulation. The supply and return contacts may also be reversed. In the stimulation exemplary stimulation methodology illustrated in FIG. 18A, the IPG 200 supplies stimulation energy to contact 114b-1 (or contact 112b-2), while contact 112b-2 (or contact 114b-1) forms part of the return path for the stimulation energy, which results in a hybrid of axial vector and radial vector stimulation. Turning to the exemplary stimulation methodology illustrated in FIG. 18B, the IPG 200 supplies stimulation energy to contact 114b-3, while contacts 112b-3 and 12b-8 form part of the return path for the stimulation energy, which also results in predominantly axial vector stimulation. The nerve cuff 102b" illustrated in FIG. 17B may be use in similar methodologies, albeit with connected pairs of contacts used for stimulation energy supply or return in some instances.

Figure 19:
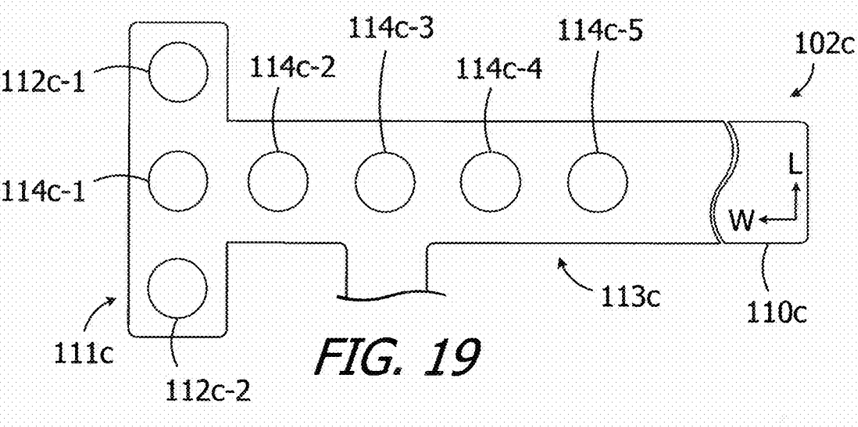
FIG. 19 is a front view of a nerve cuff in accordance with one embodiment of a present invention in an unfurled state.

The exemplary nerve cuff 102c in FIG. 19 is similar to nerve cuff 102 in that nerve cuff 102c includes a cuff body, with a front layer and a rear layer, and a plurality of contacts that are formed by conductive members and openings in the front layer. Here, however, the nerve cuff 102c lacks relatively wide contacts and includes a cuff body 110c that is T-shaped and has a first portion 111c that extends in the length direction and a second portion 113c that extends in the width direction and that is perpendicular, but is not necessarily, to the first portion 111c. Contacts 112c-1 and 112c-2 are located on the cuff first portion 111c and are spaced in length direction. A contact 114c1 is located on the cuff first portion 111c between the contacts 112c-1 and 112c-2, and a plurality of contacts 114c-2 to 114c-5 are located on the cuff body second portion 113c. Put another way, the contacts 112c-1, 112c-2 and 114c1 form a column that extends in the length direction, and the contacts 114c-1 to 114c-5 form a row that may be, but is not necessarily, perpendicular to the column. The contacts 114c-1 to 114c-5 together function in a manner similar to the contacts 114-1 to 114-5 above.

The exemplary nerve cuff 102c may be used in, for example, a stimulation methodology similar to that illustrated in FIG. 15k Here, the IPG 200 may supply stimulation energy to contacts 114c-1 to 114c-5, while contacts 112c-1 and 112-c2 form part of the return path for the stimulation energy. In another exemplary method, the IPG 200 may supply stimulation energy to contact 114c1, while one or both of contacts 112c-1 and 112-c2 form part of the return path for the stimulation energy.

Figure 20:
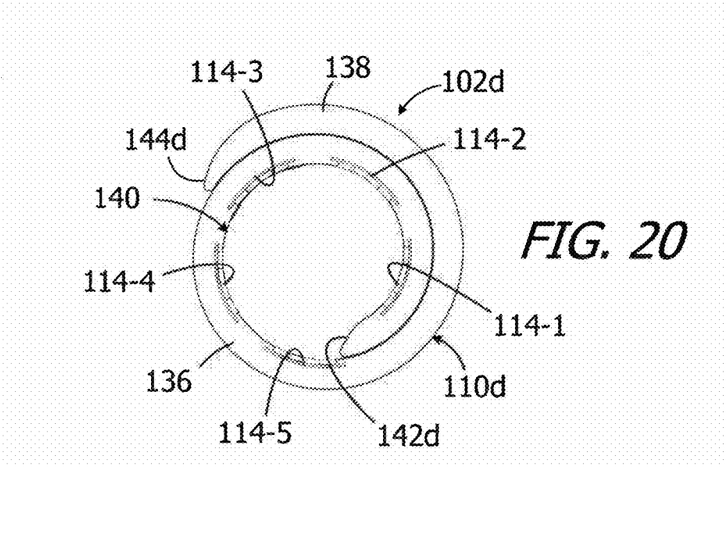
FIG. 20 is a section view of a nerve cuff in accordance with one embodiment of a present invention.

Turning to FIG. 20, the exemplary nerve cuff 102d illustrated therein is essentially identical to nerve cuff 102 and similar elements are represented by similar reference numerals. For example, the nerve cuff 102d includes a cuff body 110d, relatively wide contacts 112-1 and 112-2 and relatively narrow contacts 114-1 to 114-5. The cuff body 110d has a stimulation region 136 and a compression region 138. Here, however, the lateral ends 142d and 144d of the cuff body 110d are tapered. The tapered ends 142d and 144d eliminate what would otherwise be sharp edges and reduce the likelihood of tissue irritation.

Figure 21:
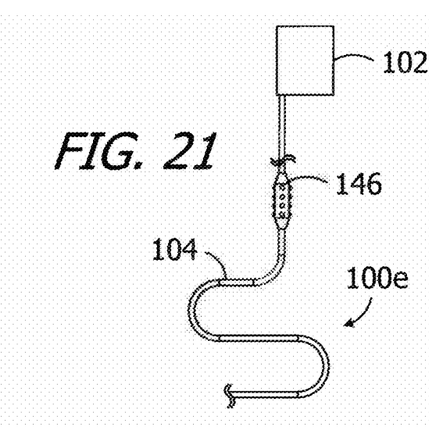
FIG. 21 is a plan view of an electrode lead in accordance with one embodiment of a present invention.
Figure 22:
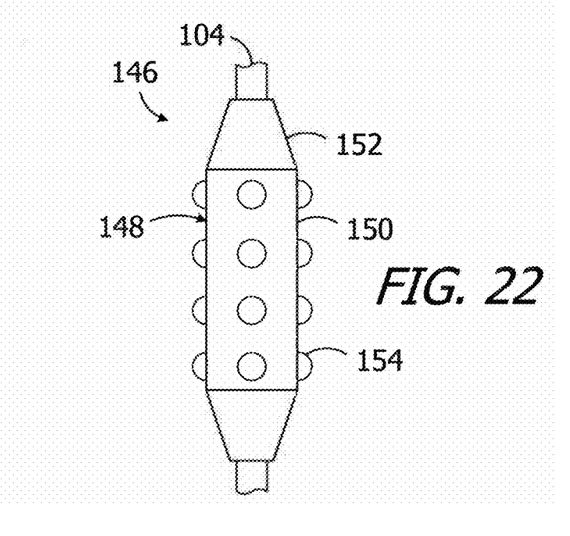
FIG. 22 is a plan view of a portion of the electrode lead illustrated in FIG. 21.

Another exemplary electrode lead is generally represented by reference numeral 100e in FIG. 21. The electrode lead 100e is substantially similar to electrode lead 100 and similar elements are represented by similar reference numerals. The electrode lead 100e includes, for example, the nerve cuff 102 and lead body 104. The electrode lead 100e also includes a suture anchor 146. Turning to FIG. 22, the exemplary suture anchor 146 includes a base 148, with a cylindrical portion 150 and tapered portions 152, and a plurality of protuberances 154.

Although the inventions disclosed herein have been described in terms of the preferred embodiments above, numerous modifications and/or additions to the above-described preferred embodiments would be readily apparent to one skilled in the art. It is intended that the scope of the present inventions extend to all such modifications and/or additions. The inventions include any and all combinations of the elements from the various embodiments disclosed in the specification. The scope of the present inventions is limited solely by the claims set forth below.

We claim:

1. An electrode lead, comprising:
an elongate lead body having a proximal end and a distal end;
a biologically compatible, elastic, electrically insulative cuff body affixed to the distal end of the lead body, the cuff body being configured to be circumferentially disposed around a nerve, having a pre-set furled state that defines an inner lumen with a longitudinal axis, being movable to an unfurled state, and defining a length, a length direction, a width in the unfurled state that is greater than the length, and a width direction;
first and second electrically conductive contacts carried by the cuff body that are spaced from one another in the length direction and that extend in the width direction to such an extent that both of the first and second electrically conductive contacts extend more than 360° around the longitudinal axis of the cuff body inner lumen when the cuff body is in the pre-set furled shape;
a plurality of intermediate electrically conductive contacts carried by the cuff body that are shorter than the first and second electrically conductive contacts in the width direction, are spaced from one another in the width direction and are located between the first and second electrically conductive contacts; and
a plurality of electrical conductors extending through the lead body from at least some of the electrically conductive contacts to the proximal end of the lead body.

2. An electrode lead as claimed in claim 1, further comprising:
a plurality of lead connector terminals at the proximal end of the lead body that are connected to the plurality of electrical conductors.

3. An electrode lead as claimed in claim 1, wherein
the first and second electrically conductive contacts are the same length.

4. An electrode lead as claimed in claim 1, wherein
the first and second electrically conductive contacts are the only two electrically conductive contacts that extend more than 360° around the longitudinal axis of the cuff body inner lumen when the cuff body is in the pre-set furled shape.

5. An electrode lead as claimed in claim 1, wherein
the first and second electrically conductive contacts are parallel to one another.

6. An electrode lead as claimed in claim 1, wherein
the plurality of intermediate electrically conductive contacts comprises at least five intermediate electrically conductive contacts.

7. An electrode lead as claimed in claim 1, wherein
all of the intermediate electrically conductive contacts are equidistant from the first and second electrically conductive contacts.

8. An electrode lead as claimed in claim 1, wherein
not all of the intermediate electrically conductive contacts are equidistant from the first and second electrically conductive contacts.

9. An electrode lead as claimed in claim 1, wherein
the cuff body includes a stimulation region on which all of the contacts are located and a compression region that wraps around the stimulation region when the cuff body is in the pre-set furled shape.

10. A method, comprising:
placing the cuff body of the electrode lead claimed in claim 1 on either one of the hypoglossal nerve (HGN) trunk and the branch of the HGN that is responsible for protruding the tongue (HGN GM branch);
applying stimulation energy to the HGN trunk with at least some of the electrically conductive contacts in instances where the cuff body is on the HGN trunk; and
applying stimulation energy to the HGN GM branch with at least some of the electrically conductive contacts in instances where the cuff body is on the HGN GM branch.

11. A method as claimed in claim 10, wherein
applying stimulation energy to the HGN GM branch comprises applying stimulation energy to the HGN GM branch with all of the intermediate electrically conductive contacts and returning the stimulation energy with at least one of the first and second electrically conductive contacts.

12. A method as claimed in claim 10, wherein
applying stimulation energy to the HGN trunk comprises applying stimulation energy to the HGN trunk with at least one of the intermediate electrically conductive contacts and returning the stimulation energy with at least one of the intermediate electrically conductive contacts.

13. A method as claimed in claim 10, wherein
applying stimulation energy to the HGN trunk comprises applying stimulation energy to the HGN trunk with at least one of the intermediate electrically conductive contacts and returning the stimulation energy with at least one of the first and second electrically conductive contacts and at least one of the intermediate electrically conductive contacts.

* * * * *